(12) United States Patent
Iguchi et al.

(10) Patent No.: US 10,702,702 B2
(45) Date of Patent: *Jul. 7, 2020

(54) LIGHT IRRADIATION SUBSTRATE AND LIGHT IRRADIATION DEVICE

(71) Applicant: SHARP KABUSHIKI KAISHA, Sakai, Osaka (JP)

(72) Inventors: Katsuji Iguchi, Sakai (JP); Jun Mori, Sakai (JP); Tohru Nakanishi, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/553,816

(22) PCT Filed: Jan. 20, 2016

(86) PCT No.: PCT/JP2016/051614
§ 371 (c)(1),
(2) Date: Aug. 25, 2017

(87) PCT Pub. No.: WO2016/136340
PCT Pub. Date: Sep. 1, 2016

(65) Prior Publication Data
US 2018/0043177 A1      Feb. 15, 2018

(30) Foreign Application Priority Data

Feb. 26, 2015   (JP) ................... 2015-036925

(51) Int. Cl.
*A61N 5/06*      (2006.01)
*A61B 90/00*     (2016.01)

(52) U.S. Cl.
CPC ...... *A61N 5/0616* (2013.01); *A61B 2090/036* (2016.02); *A61N 2005/0626* (2013.01);
(Continued)

(58) Field of Classification Search
None
See application file for complete search history.

(56) References Cited

U.S. PATENT DOCUMENTS 5,616,140 A    4/1997 Prescott
5,913,883 A    6/1999 Alexander et al.
(Continued)

FOREIGN PATENT DOCUMENTS

CN    103296017 A    9/2013
JP    2003-526391 A  9/2003
(Continued)

OTHER PUBLICATIONS

Kuniyuki Morimoto, et al., 'Photodynamic Therapy Using Systemic Administration of 5-Aminolevulinic Acid and a 410-nm Wavelength Light-Emitting Diode for Methicillin-Resistant *Staphylococcus aureus*-Infected Ulcers in Mice', PLOS ONE, Aug. 2014, vol. 9, Issue 8 e105173.

*Primary Examiner* — Carl H Layno
*Assistant Examiner* — Manolis Pahakis
(74) *Attorney, Agent, or Firm* — ScienBiziP, P.C.

(57) ABSTRACT

A light irradiation substrate is provided which can cope with cases of emergency and which is capable of optimum irradiation with therapeutic light regardless of the shape or size of affected parts while keeping a lid on cost. The center-to-center distance between two adjacent LED chips (13) facing each other across the boundary between two unit substrates (7) adjacent to each other in an X direction or (a Y direction) and belonging to the respective unit substrates (7) is twice or less as long as the center-to-center distance between two LED chips (13) adjacent to each other in the X direction (or the Y direction) within each of the unit substrates (7). Each of the unit substrates (7) includes a connection section (10) that provides external connection of
(Continued)

wires (12). The connection section (10) is provided on a back surface of a flexible substrate (6).

4 Claims, 6 Drawing Sheets

(52) U.S. Cl.
CPC .............. *A61N 2005/0652* (2013.01); *A61N 2005/0659* (2013.01); *A61N 2005/0661* (2013.01); *A61N 2005/0663* (2013.01)

(56) References Cited

U.S. PATENT DOCUMENTS

| | | | |
|---|---|---|---|
| 6,096,066 A | 8/2000 | Chen et al. | |
| 6,290,713 B1 | 9/2001 | Russell | |
| 6,443,179 B1* | 9/2002 | Benavides | F15C 5/00 137/454.2 |
| 6,459,919 B1* | 10/2002 | Lys | A61N 5/0616 315/291 |
| 6,596,016 B1* | 7/2003 | Vreman | A61N 5/0621 128/903 |
| 8,097,926 B2* | 1/2012 | De Graff | H01L 27/14687 257/419 |
| 8,886,334 B2* | 11/2014 | Ghaffari | A61B 1/00082 607/115 |
| 9,289,132 B2* | 3/2016 | Ghaffari | A61B 1/00082 |
| 2005/0104059 A1* | 5/2005 | Friedman | A61M 25/1011 257/40 |
| 2005/0116667 A1* | 6/2005 | Mueller | E04F 13/08 315/312 |
| 2007/0208396 A1* | 9/2007 | Whatcott | A61N 5/0613 607/88 |
| 2008/0042558 A1* | 2/2008 | Buchhauser | H01L 27/3225 313/504 |
| 2008/0269849 A1* | 10/2008 | Lewis | A61N 5/0613 607/91 |
| 2009/0018622 A1* | 1/2009 | Asvadi | A61N 5/0621 607/91 |
| 2010/0045175 A1* | 2/2010 | Mathai | H01L 27/3209 313/504 |
| 2010/0045189 A1* | 2/2010 | Storch | H01L 51/50 315/149 |
| 2010/0076527 A1* | 3/2010 | Hammond | G09F 9/33 607/88 |
| 2010/0106077 A1 | 4/2010 | Rabin et al. | |
| 2010/0259928 A1* | 10/2010 | Ou Yang | F21K 9/00 362/235 |
| 2011/0181494 A1* | 7/2011 | Wong | G09F 9/33 345/1.3 |
| 2011/0181495 A1* | 7/2011 | Chu | G09F 9/33 345/1.3 |
| 2011/0195532 A1* | 8/2011 | Lerman | H01L 25/0753 438/27 |
| 2011/0222286 A1 | 9/2011 | Oba et al. | |
| 2011/0242771 A1* | 10/2011 | Bhattacharya | H05K 1/038 361/733 |
| 2012/0165759 A1* | 6/2012 | Rogers | A61B 5/6867 604/264 |
| 2012/0253433 A1* | 10/2012 | Rosen | A61N 5/0621 607/91 |
| 2012/0320581 A1* | 12/2012 | Rogers | H01L 24/24 362/235 |
| 2013/0144364 A1 | 6/2013 | Wagenaar et al. | |
| 2013/0229802 A1 | 9/2013 | Fukushima et al. | |
| 2013/0258662 A1* | 10/2013 | Treanton | F21S 2/005 362/235 |
| 2013/0301264 A1* | 11/2013 | Van Gompel | F21S 2/005 362/236 |
| 2013/0304019 A1* | 11/2013 | Cooper | A61N 5/062 604/501 |
| 2014/0207215 A1* | 7/2014 | Fiset | A61N 5/0614 607/94 |
| 2014/0226329 A1* | 8/2014 | Oraw | H01L 25/0753 362/235 |
| 2014/0268780 A1* | 9/2014 | Wang | F21V 19/003 362/249.06 |
| 2015/0188082 A1* | 7/2015 | Rohatgi | H01L 51/5253 257/40 |
| 2015/0194123 A1* | 7/2015 | Lee | G02B 3/0037 345/1.3 |
| 2015/0221569 A1* | 8/2015 | Palm | H01L 24/82 257/690 |
| 2015/0267907 A1* | 9/2015 | Thompson | F21V 23/06 362/249.06 |
| 2015/0290470 A1* | 10/2015 | Tapper | A61N 5/0616 607/91 |
| 2016/0035924 A1* | 2/2016 | Oraw | H01L 31/0508 136/244 |
| 2016/0076708 A1* | 3/2016 | Shirilla | F21S 2/005 362/235 |
| 2016/0123569 A1* | 5/2016 | Cummings | F21S 2/005 362/249.02 |
| 2016/0267836 A1* | 9/2016 | Meersman | G09G 3/32 |
| 2017/0118838 A1* | 4/2017 | Williams | H05K 3/4691 |

FOREIGN PATENT DOCUMENTS

| | | |
|---|---|---|
| JP | 2011-210705 A | 10/2011 |
| WO | 0114012 A1 | 3/2001 |
| WO | 2008144157 A1 | 11/2008 |
| WO | 2012023086 A1 | 2/2012 |
| WO | 2012/073543 A1 | 6/2012 |

\* cited by examiner

LIGHT IRRADIATION SUBSTRATE AND LIGHT IRRADIATION DEVICE

TECHNICAL FIELD

The present invention relates to a light irradiation substrate and a light irradiation device that mainly irradiate an affected part of the skin of a human or an animal for treatment purposes, esthetic purposes, or similar purposes.

BACKGROUND ART

Light irradiation has been utilized for various purposes such as the purpose of treating diseases such as neonatal jaundice, psoriasis, and acne, the purpose of alleviating pain, and esthetic purposes. Specifically, green light and bluish white light have been used for treatment of neonatal jaundice. Ultraviolet light has been used for treatment of psoriasis. Blue Light, red light, and yellow light have been used for treatment of acne. In this way, various types of light source have been used depending on the purposes.

For example, in the case of a light source such as an excimer lamp or an arc lamp, an affected part is placed at a certain distance from a fixed light source and irradiated with therapeutic light. However, in a case where such a lamp type of light source is used, there is concern for various types of side effect on normal sites, as the irradiation area is so large that the therapeutic light strikes other parts as well as the affected part. This makes it necessary to take some sort of shielding measure to prevent the normal sites from being irradiated with the therapeutic light, requiring time and effort for treatment. For example, in the case of treatment of a disease affecting a part of a face, a sleeping mask (blindfold) is needed to protect the eyes, which are normal sites. Furthermore, a mask designed to expose only the affected part of the face is needed to protect the normal sites of the face. Further, the patient is required to keep standing at attention for several tens of minutes while being placed under restraint for treatment. This is certainly not a good experience even for treatment purposes. Further, in the case of an affected part having a bent surface, as in the case of an arm or a leg, a lamp type of irradiation device may force the patient to take an uncomfortable posture, depending on the site such as the front side, the back side, or the lateral side. Further, irradiation intensities vary from position to position of the affected part having a bent portion, depending on the angle and distance of the affected part with respect to the lamp. This may make it difficult to uniformly irradiate the whole affected part with the therapeutic light. Furthermore, a device including such a lamp type of light source comes with many attachments such as a power source and a cooling device and, as is bulky. Such a device requires a large installation space and bears a high price. Therefore, such a device can only be installed in a facility for treatment, making it necessary to attend the facility for treatment.

Meanwhile, irradiation light from a device including a laser as a light, source forms a spotlight whose irradiation area is small. Therefore, irradiation of a large-area affected part as a whole with therapeutic light requires the spotlight to be passed over the affected part. This undesirably makes the device complex and expensive.

Further, a type of device that uses an optical fiber for planar irradiation with therapeutic light is comparatively low in efficiency in the sending of light into the optical fiber and therefore inevitably low in irradiation power. Such a device is only suited for comparatively long-term treatment.

Against this backdrop, there has been a demand for a flexible substrate including a light source that makes it possible to keep a certain distance from an affected part and cover the affected part in conformance with the shape of the affected part. In response to such a demand, several technologies such as those described below have been proposed.

For example, PTL 1 discloses a light irradiation device in which a laser and an LED are disposed as light-emitting light sources on a flexible substrate and which is wound around an affected part for use. PTL 2 discloses a facial light irradiation device in which LEDs are disposed as light-emitting light sources on a flexible substrate and which covers a face for use. PTL 3 discloses a flexible light irradiation device in which a large number of LEDs serving as light-emitting light sources are arranged on a flexible substrate and which is wound around an affected part for light irradiation. PTL 4 discloses a light irradiation device, premised on application to a head, in which an LED serving as a light-emitting light source is disposed inside a hat. PTL 5 discloses a light irradiation device in which a LED serving as a light-emitting light source is disposed on a flexible substrate and which, with a light-transmitting substance interposed between an affected part and the LED, can transmit, to the affected part, light emitted by the LED.

NPL 1 gives a description of a method for treating methicillin-resistant *Staphylococcus Aureus* (MRSA) infected cutaneous ulcers with near-ultraviolet light. This method of treatment is a therapy by which a part infected with antibiotic-resistant *Staphylococcus Aureus* is irradiated with near-ultraviolet light (at a wavelength of about 410 nm) to kill the bacteria. This method of treatment is based on a process by which systemically-administered 5-aminolevulinic acid (ALA) is metabolized and accumulated in protoporphyrin IX (hereinafter referred to as "PpIX") in the bacteria and the bacteria are destructed from within the cells by active oxygen generated when PpIX is degraded by near-ultraviolet light. This method of treatment is a technique that has no side effects on the cells of an affected part per se and makes it possible to kill antibiotic-resistant bacteria without inducing antibiotic contamination. As such, this method of treatment has a broad range of applications and is considered to be very highly promising.

The configurations disclosed in PTLs 1 to 5 are expected to reduce various burdens such as those mentioned above on patients by covering an affected part, for example, with a flexible substrate including an LED and by irradiating the affected part with therapeutic light and to be able to uniformly irradiate even an affected part having a bent portion with therapeutic light. Further, it is conceivable that the configurations disclosed in PTLs 1 to 5 may be used to achieve the method of treatment disclosed in NPL 1.

CITATION LIST

Patent Literature

PTL 1: U.S. Pat. No. 5,616,140
PTL 2: U.S. Pat. No. 5,913,883
PTL 3: International Publication No. WO/2001/014012 A1 (published on Mar. 1, 2001)
PTL 4: International Publication No. WO/2008/144157 A1 (published on Nov. 27, 2008)
PTL 5: International Publication No. WO/2012/023086 A1 (published on Feb. 23, 2012)

Non Patent Literature

NPL 1: Kuniyuki Morimoto and six more authors, 'Photodynamic therapy using systemic administration of 5-aminolevulinic acid and a 410-nm wavelength light-emitting diode for methicillin-resistant *Staphylococcus aureus*-infected ulcers in mice', *PLOS ONE*, Aug. 2014, Volume 9, Issue 8 e105173, (published on Aug. 20, 2014)

SUMMARY OF INVENTION

Technical Problem

However, the aforementioned conventional technologies have the following problems. Affected parts to be irradiated with therapeutic light not only vary in shape and size depending on the patients, but also vary in shape and size depending on the sites of the affected parts. The only way to cope with such affected parts of various shapes and sizes is to custom-make a flexible substrate including an LED or a flexible member for each case, which ends up bearing a very high price. Further, since the making starts after confirmation of the shape and size of an affected part, it takes time to deliver the product, making it too late for emergency treatment.

Meanwhile, an attempt to impart versatility, for example, to flexible substrates including LEDs raises the need to manufacture in advance a large number of flexible substrates of various sizes including very large flexible substrates, regardless of whether the flexible substrates are actually used. In such a case, it is anticipated that a large number of flexible substrates are wasted, as they are not actually used, and there is no choice but to have a large number of flexible substrates in stock. This imposes a heavy burden on the manufacturer's side and leads to a significant decrease in economic efficiency.

It is an object of the present invention to provide a light irradiation substrate and a light irradiation device that are capable of optimum irradiation with therapeutic light regardless of the shape or size of affected parts at the lowest possible cost even in cases of emergency. It is another object of the present invention to provide light treatment with reduced burden on users through efficient and uniform irradiation with therapeutic light while minimizing the side effects of irradiation with therapeutic light on normal sites that do not require irradiation with therapeutic light.

Solution to Problem

In order to solve the foregoing problems, a light irradiation substrate of the present invention is a light irradiation substrate including: a flexible substrate composed of a plurality of unit substrates that are detachable; a plurality of light-emitting elements provided in a matrix on a first surface of the flexible substrate for each unit substrate; and wires through which electrical currents flow to each separate light-emitting element, the wires being provided on the first surface of the flexible substrate for each unit substrate, wherein a center-to-center distance between two adjacent light-emitting elements facing each other across a boundary between two of the unit substrates adjacent to each other in first direction and belonging to the respective unit substrates is twice or less as long as a center-to-center distance between two light-emitting elements adjacent to each other in the first direction within each of the unit substrates, and each of the unit substrates includes a connection section that provides external connection of the wires, the connection section being provided on a second surface of the flexible substrate opposite to the first surface.

According to the foregoing configuration, the plurality of light-emitting elements are provided in a matrix on the first surface of the flexible substrate for each unit substrate; and the wires through which electrical currents flow to each separate light-emitting element are provided on the first surface of the flexible substrate for each unit substrate. This allows the unit substrates to have substantially the same light irradiation intensity. Moreover, according to the foregoing configuration, a reduction in uniformity of light irradiation intensity at the boundary between two of the unit substrates adjacent to each other in the first direction or the boundary between two of the unit substrates disposed to be adjacent to each other in the first direction after having been detached can be kept within a predetermined range. Therefore, the light irradiation intensity at the joint between the unit substrates can be made substantially the same as that within each of the unit substrates.

Further, the flexible substrate of the light irradiation substrate includes a plurality of unit substrates that are detachable from one another. Therefore, for example in the case of an affected part that is smaller in size than the flexible substrate, at least one of the unit substrates can be detached from the flexible substrate and used as a light irradiation substrate to optimally irradiate the affected part with therapeutic light. Meanwhile, for example in the case of an affected part that is larger in size than the flexible substrate, two or more of these light irradiation substrates can be combined or at least one of the unit substrates and the light irradiation substrate can be combined to optimally irradiate the affected part with therapeutic light.

Therefore, unlike in the conventional case, an attempt to impart versatility to light irradiation substrates does not raise the need to manufacture in advance a large number of flexible substrates of various sizes including very large flexible substrates.

Furthermore, the foregoing configuration makes it possible to completely prevent the connection section from hindering light irradiation. Further, the foregoing configuration makes it possible to, in performing light irradiation, easily bring the spacer used and the irradiation substrate into intimate contact with each other.

Therefore, the foregoing configuration makes it possible to achieve a light irradiation substrate that is capable of optimum irradiation with therapeutic light regardless of the shape or size of affected parts at the lowest possible cost even in cases of emergency. Furthermore, the foregoing configuration makes it possible to achieve light treatment with reduced burden on users through efficient and uniform irradiation with therapeutic light while minimizing the side effects of irradiation with therapeutic light on normal sites that do not require irradiation with therapeutic light.

In order to solve the foregoing problems, a light irradiation device of the present invention is a light irradiation device including: the light irradiation substrate; a power source section including a plurality of unit power sources; and a control section that adjusts an emission intensity of each of the unit substrates by controlling the power source section, wherein each of the unit substrates has a wire connected to a corresponding one of the plurality of unit power sources.

The foregoing configuration makes it possible to achieve a light irradiation device that is capable of optimum irradiation with therapeutic light regardless of the shape or size of affected parts at the lowest possible cost even in cases of emergency.

Advantageous Effects of Invention

An aspect of the present invention makes it possible to achieve a light irradiation substrate and a light irradiation device which can cope with cases of emergency and which are capable of optimum irradiation with therapeutic light regardless of the shape or size of affected parts while keeping a lid on cost. Furthermore, the aspect of the present invention makes it possible to achieve light treatment with reduced burden on users through efficient and uniform irradiation with therapeutic light while minimizing the side effects of irradiation with therapeutic light on normal sites that do not require irradiation with therapeutic light.

DESCRIPTION OF EMBODIMENTS

In the following, embodiments of the present invention are described in detail with reference to the drawings. Note, however, that the dimensions, materials, shapes, relative arrangements, method of processing, and the like of configurations described in these embodiments are merely embodiments and the scope of the invention should not be narrowly interpreted because of these embodiments. Furthermore, the drawings are schematic, and the ratios of dimensions and the shapes are different from what they actually are.

Embodiment 1

An embodiment of the present invention is described with reference to FIGS. 1 to 3.

Figure 1:
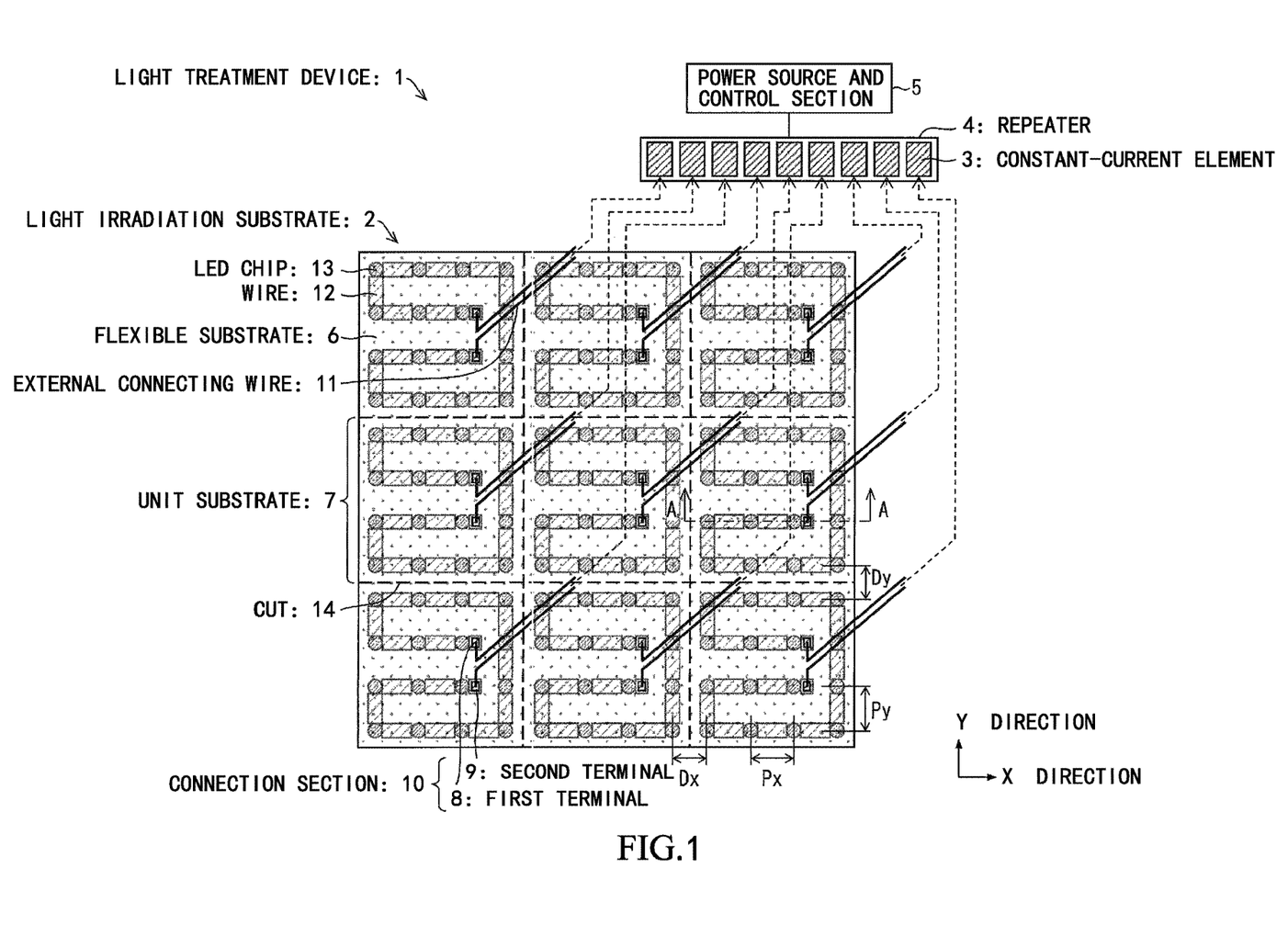
FIG. 1 schematically illustrates a configuration of a light treatment device according to an embodiment of the present invention.

FIG. 1 schematically illustrates a configuration of a light treatment device 1. As illustrated in FIG. 1, the light treatment device 1 includes a light irradiation substrate 2, a repeater 4, and a power source and control section 5. The repeater 4 is a distributor that supplies a constant current to each unit substrate 7. The power source and control section supplies power to the repeater 4 and controls the repeater 4. It should be noted that the repeater 4 includes as many constant-current elements 3 as the unit substrates 7.

(Light Irradiation Substrate)

As illustrated in FIG. 1, the light irradiation substrate 2 includes a flexible substrate 6 composed of a plurality of unit substrates 7 that are detachable from one another. In the present embodiment, the flexible substrate 6 used is a polyimide sheet measuring 120 mm per side, and the polyimide sheet is composed of nine unit substrates 7 each measuring 40 mm per side. FIG. 1 illustrates a lower surface of the flexible substrate 6. The lower surface is provided with connection sections 10 each including a first terminal 8 and a second terminal 9 provided on a back-surface wire described below, and the connection sections 10 are connected to the constant-current elements 3 of the repeater 4 via external connecting wires 11, respectively. Meanwhile, an upper surface of the flexible substrate 6 opposite to the lower surface of the flexible substrate 6 is provided with a plurality of LED chips (light-emitting diode chips) 13 serving as light-emitting elements and with wires 12 through which electrical currents flow to each separate LED chip 13. These LED chips 13 and these wires 12 are repeatedly provided for each unit substrate 7. It should be noted that since FIG. 1 illustrates the lower surface of the flexible substrate 6, the wires 12 and the LED chips 13, which are provided on the upper surface of the flexible substrate 6, cannot be seen from the lower surface of the flexible substrate 6; however, FIG. 1 illustrates the wires 12 and the LED chips 13 to facilitate understanding.

Each of the LED chips 13 used in the present embodiment is almost square in shape and, as such, has a difference of about 1% in light irradiation intensity between the X and Y directions illustrated in FIG. 1. Therefore, the arrangement pitches between LED chips 13, i.e. the distance from the center of an LED chip 13 to the center of an adjacent LED chip 13 in an array direction (X or Y direction), are the same for both the X and Y directions. Specifically, in the present embodiment, the pitches Px between LED chips 13 in the X direction on the unit substrates 7 and the pitches Py between LED chips 13 in the Y direction on the unit substrates 7 are both 10 mm. Moreover, the center-to-center distance Dx between two adjacent LED chips 13 facing each other across the boundary between two unit substrates 7 adjacent to each other in the X direction and belonging to the respective unit substrates 7 and the center-to-center distance Dy between two adjacent LED chips 13 facing each other across the boundary between two unit substrates 7 adjacent to each other in the Y direction and belonging to the respective unit substrates 7 are both 10 mm. The flexible substrate 6 has cuts 14 formed in the X and Y directions by perforation so that two adjacent unit substrates 7 can be easily detached from each other at the boundary.

As the flexible substrate 6 for forming the unit substrates 7 by detaching becomes larger, the light irradiation substrate 2 it forms can become larger in area However, the execution of a series of operations of actually mounting LED chips 13 and forming a protective layer over the LED chips imposes restrictions on the manufacturing apparatus used. This makes it impossible to fabricate an unlimitedly large flexible substrate 6. Given these circumstances, in the case of fabrication of a light irradiation substrate that is larger in size than can be manufactured under the restrictions on the manufacturing apparatus used or the like, a large light irradiation substrate can be formed by combining. For example, four flexible substrates each measuring 120 mm per side can be combined, for example, into a light irradiation substrate having a size of 120 mm by 480 mm or a light irradiation substrate having a size of 240 mm by 240 mm.

Figure 2:
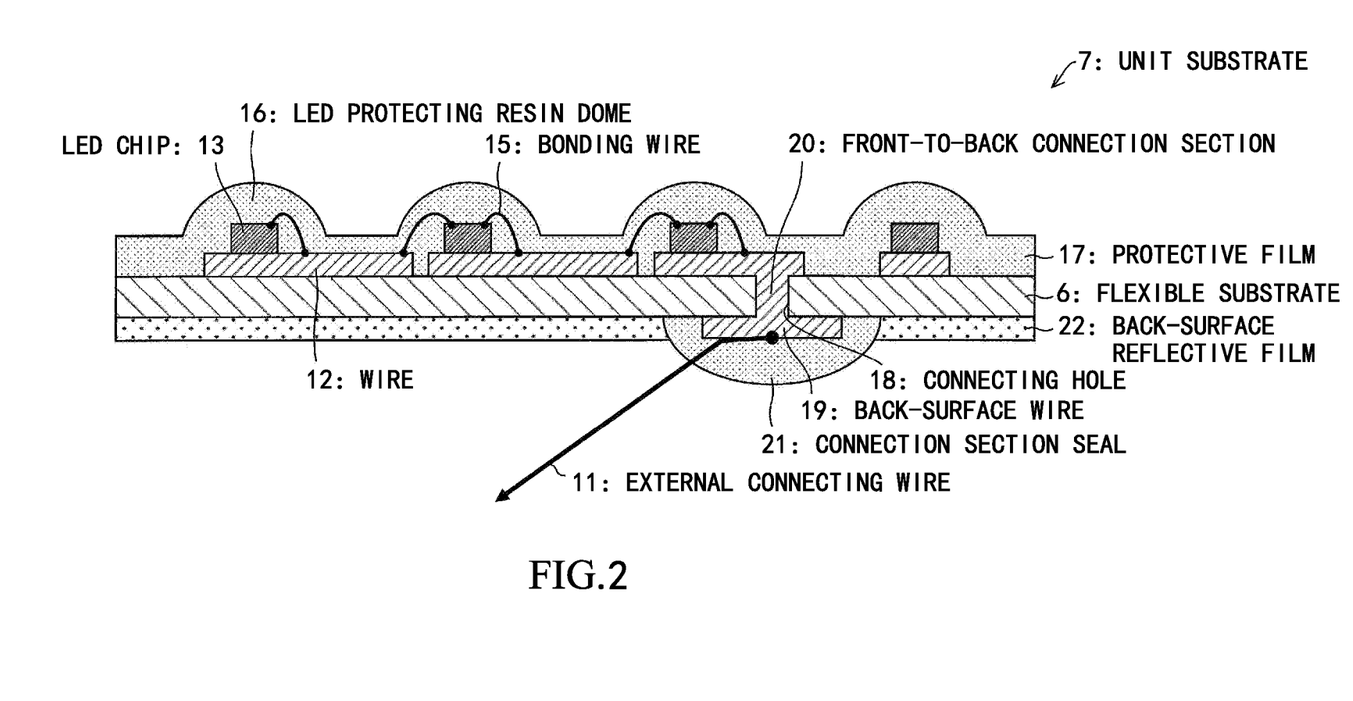
FIG. 2 is a cross-sectional view of a light irradiation substrate of the light treatment device illustrated in FIG. 1 as taken along line A-A.

FIG. 2 is a cross-sectional view of the light irradiation substrate 2 illustrated in FIG. 1 as taken along line A-A and also a cross-sectional view of a unit substrate 7. As illustrated FIG. 2, wires 12 are formed on the flexible substrate 6 of the unit substrate 7, and LED chips 13 serving as light sources are mounted on the wires 12, respectively, with bonding wires 15 connecting the wires 12 and the LED chips 13. A part of each of the wires 12, the LED chip 13, and the bonding wires 15 are covered with an LED protecting resin dome 16, and the whole of the remaining part of the wire 12 that is not covered with the LED protecting resin dome 16 is coated with a protective film 17. The flexible substrate is provided with a connecting hole 18 bored through the flexible substrate 6, and a wire 12 on the upper surface of the flexible substrate 6 and a back-surface wire 19 on the lower surface of the flexible substrate 6 are connected by a front-to-back wire connection section 20 via the connecting hole 18. A back-surface wire 19 provided on the lower surface of each unit substrate 7, a connection section 10 including a first terminal 8 and a second terminal 9 provided on the back-surface wire 19, and a part of an external connecting wire 11 connected to the connection section 10 are covered with a connection section seal 21. Furthermore, a back-surface reflective film 22 is provided on the lower surface of the unit substrate 7 excluding the part where the connection section seal 21 is formed. Because the back-surface reflective film 22 is intended to prevent light from leaking toward the lower surface of the unit substrate 7 when the LED chips 13 are on, it is preferable that the back-surface reflective film 22 cover as wide an area as possible on the lower surface of the unit substrate 7.

By supplying power to such a unit substrate 7 via the external connecting wire 11 with the upper surface facing an affected part, the unit substrate 7 can be used as a light irradiation substrate to irradiate the affected part with light.

In the unit substrate 7, the LED chips 13 are provided on the upper surface of the unit substrate 7, and the connection section 10 for supplying power via the external connecting wire 11 is provided on the lower surface of the unit substrate 7. This makes it possible to completely prevent the means for supplying an electrical current to the unit substrate 7 (e.g. the connection section 10 including a first terminal 8 and a second terminal 9, the external connecting wire 11, the back-surface wire 19, the front-to-back wire connection section 20, and the like) from hindering light irradiation at the time of therapy.

Further, since the wires 12, the plurality of LED chips 13, and the current supply means are repeatedly provided for each unit substrate 7, there is no wire routed across the boundary between unit substrates 7, so that the unit substrates 7 can be detached from each other.

The light irradiation substrate 2 may be used alone without being cut or a plurality of the light irradiation substrates 2 may be used in combination, depending on the size of the affected part. The light irradiation substrate 2 may be used with an unnecessary unit substrate 7 cut away therefrom or one or more unit substrates 7 into which the light irradiation substrate 2 has been cut may be used alone or in combination as a light irradiation substrate, depending on the size of the affected part. Furthermore, the light irradiation substrate 2 and a unit substrate 7 may be used in combination as a light irradiation substrate. As stated above, the use of the light irradiation substrate 2 makes it possible to cope with small-to-large-area affected parts and regardless of the size of the affected parts.

(Flexible Substrate)

Although, in the present embodiment, the flexible substrate 6 used is a polyimide sheet (polyimide film) measuring 120 mm per side and having a thickness of 50 µm, this is not intended to limit the size thereof, the thickness thereof, or the material of which it is made. The size thereof needs only be appropriately determined in consideration of a subsequent step, and the thickness thereof can be appropriately determined as long as insulation properties, strength, and flexibility can be ensured. Further, as for selection of material, any material can be used as long as it is an insulating material that has the required strength and flexibility.

(Wire)

Wires 12 and a back-surface wire 19 are provided on the upper and lower surfaces, respectively, of the flexible substrate 6 for each unit substrate 7. In the present embodiment, the wires 12 and the back-surface wire 19 are each formed by forming a copper plated layer on the flexible substrate 6 and then coating the copper plated layer with a silver plated layer. That is, in the present embodiment, the wires 12 and the back-surface wire 19 used are silver-plated copper wires. However, without being limited to such silver-plated copper wires, the wires 12 and the back-surface wire 19 may alternatively be wires made of a material such as aluminum.

(LED Chip)

Figure 3:
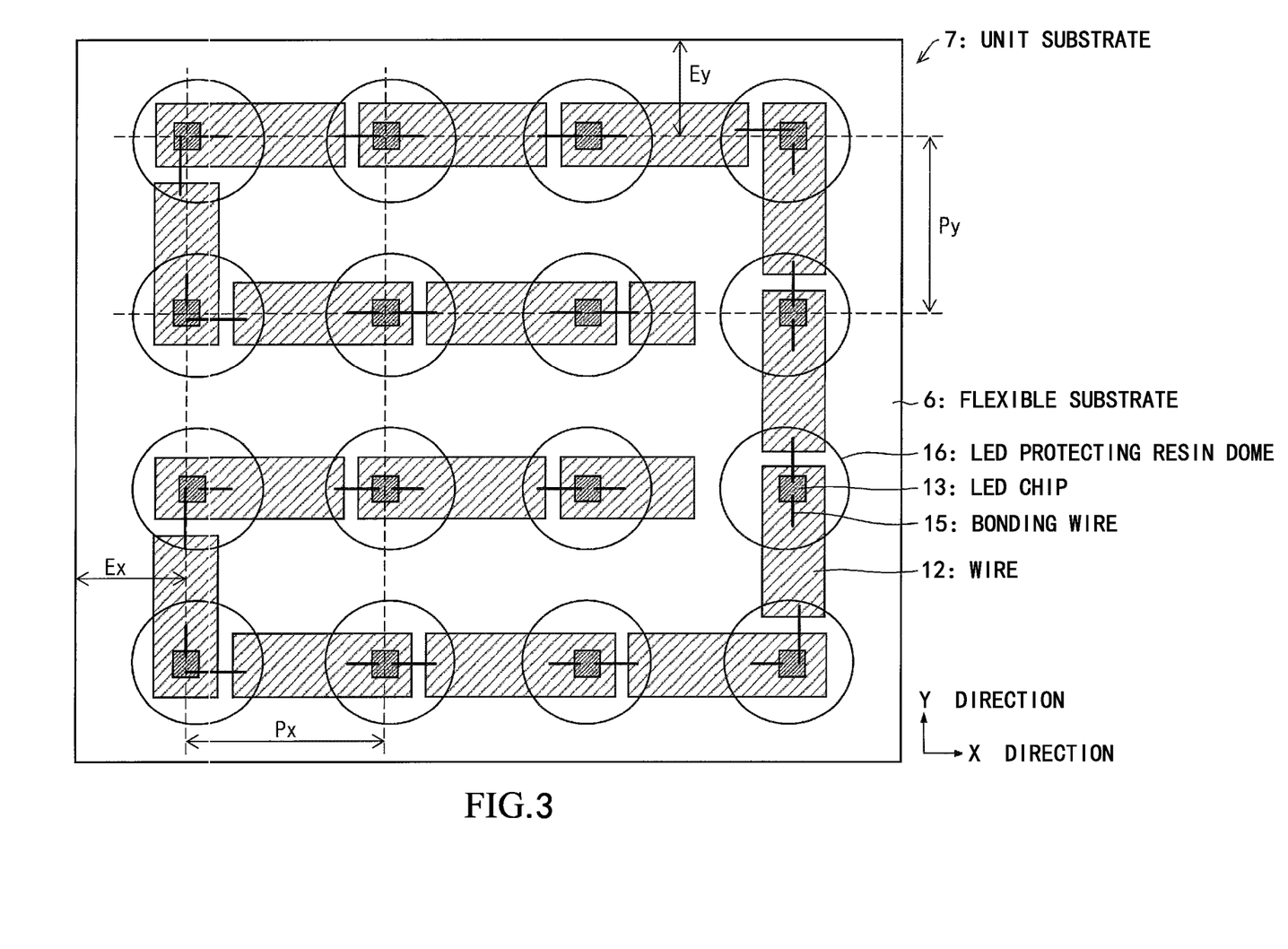
FIG. 3 illustrates an example arrangement of wires and LED chips provided on an upper surface of a unit substrate of the light treatment device illustrated in FIG. 1.

FIG. 3 illustrates an example arrangement of wires 12 and LED chips 13 provided on an upper surface of a unit substrate 7.

As illustrated in FIG. 3, in the present embodiment, a total of sixteen LED chips 13 on one unit substrate 7 are connected in series so that all of the sixteen LED chips 13 are driven by the same electrical current. However, for example in a case where the number of LED chips 13 is large and the source voltage is too high with a serial connection alone, the LED chips 13 may be connected in parallel. It should be noted that, in that case, it is necessary to devise a wiring pattern so that the same electrical current flows through each wire.

The wavelength of light that is emitted by an LED chip 13 must be selected according to treatment purposes. In the present embodiment, gallium nitride blue-violet LED chips (with a peak wavelength of 410 nm) are used as the LED chips 13 to be applied to treatment of methicillin-resistant *Staphylococcus Aureus* (MRSA) infected cutaneous ulcers described in NFL 1. It should be noted that, when used for other treatment purposes, the LED chips 13 may for example be ultraviolet, blue, and green LED chips that are similarly gallium nitride (AlInGaN) LED chips; red, yellow, and green LED chips that are quaternary (AlGaInP) LED chips; infrared LED chips that are GaAs LED chips; or the like. Furthermore, it is alternatively possible to combine a plurality of LED chips that emit light in different wavelength ranges. Therefore, optimum LED chips can be selected for any purpose.

As for the number and size of LED chips 13, an arrangement of a large number of comparatively small LED chips is preferred to a small number of high-power LED chips for the purpose of, as in the case of light treatment, uniformly irradiating do affected part of a certain area with light. Therefore, in the present embodiment, as illustrated in FIG. 3, sixteen almost-square blue-violet LED chips each having a size of 440 µm by 550 µm are mounted as the LED chips 13 for each unit substrate of the flexible substrate 6. Each of the nine unit substrates 7 has LED chips 13 arranged in a 4 by 4 array (i.e. a 4 by 4 matrix) so that, for example, the pitches Px between LED chips 13 in the X direction on the unit substrate 7 and the pitches Py between LED chips 13 in the Y direction on the unit substrate 7 are both 10 mm. It should be noted that an arrangement of LED chips 13 in an array (i.e. a matrix) means that the LED chips 13 are placed at substantially regular pitches Px and substantially regular pitches Py within the unit substrate 7 and the pitches Px and the pitches Py may be the same as or different from each other.

A gallium nitride blue-violet LED chip of this size is highest in efficiency when it has a structure in which a nitride semiconductor layer is epitaxially grown on a sapphire substrate and both positive and negative electrodes are formed on the same surface. Therefore, the LED chips 13 are bonded onto the wires 12 with a transparent die bonding paste (not illustrated), and the wires 12 and the positive and negative electrodes of the LED chips 13 are connected via the bonding wires 15. In the present embodiment, the bonding wires 15 used are gold bonding wires. However, without being limited to such gold bonding wires, the bonding wires 15 may alternatively be silver bonding wires or aluminum bonding wires.

Meanwhile, in a case where a quaternary (AlGaInP) LED chip or a GaAs infrared LED chip is used, a substrate side of the LED chip that also serves as a lower electrode is bonded onto a wire 12 with an electrical conducting material such as a silver paste and an upper electrode is connected to another wire 12 via a bonding wire, as the LED chip has a so-called upper and lower electrode structure.

(LED Protecting Resin Dome, Protective Film, and Back-Surface Reflective Film)

An LED chip 13 and bonding wires 15 can be protected by being covered with an LED protecting resin dome 16 that is a dome-shaped resin layer. This LED protecting resin dome 16 can be fabricated by potting, but in order to ensure shape reproducibility, it should be molded from resin with a metal mold. Further, in order to ensure as much flexibility as possible, it should be made of as flexible a resin material as possible. This is because, when made of a hard resin material, the LED protecting resin dome 16 may break a bonding wire in a case where the flexible substrate 6 or the unit substrate 7 becomes bent. The protective film 17, which covers the upper surface of the flexible substrate 6 or the unit substrate 7, is intended to prevent, wires 12 from being short-circuited and, in the present embodiment, is formed by a coating of silicone resin. Meanwhile, a back-surface reflective film 22 is provided on the lower surface of the flexible substrate 6 or the unit substrate 7, and the back-surface reflective film 22 is composed of an aluminum film obtained by depositing aluminum and a resin film formed as a protective film covering the aluminum film. It should be noted that the materials of which the LED protecting resin dome 16, the protective film 17, and the back-surface reflective film 22 are made in the present embodiment are non-limiting examples.

(Structure in which Connection Section is Provided on Lower Surface of Each Unit Substrate)

In the present embodiment, as illustrated in FIGS. 1 and 2, a connection section 10 is provided on the lower surface of each unit substrate 7, and an external connecting wire 11 serving as a wire to be connected to a power source that supplies an electrical current to each unit substrate 7 is taken out from the lower surface of the unit substrate 7. For greater convenience of connection to the power source, it is preferable that the external connecting wire 11 be terminated with a socket, a plug, or the like to be easily connectable to the power source. The external connecting wire 11 is connected to a pattern of a back-surface wire 19 via a solder connection or the like. For dielectric isolation of this wire connection, it is preferable that the wire connection be coated with a connection section seal 21 made of insulating resin. It should be noted that although FIG. 2 illustrates, as an example, a case where a connection is made using only a lead wire, this does not imply any limitation. A connector or the like for connecting a lead wire may be placed in each unit substrate 7.

The foregoing configuration makes it possible to completely prevent the means for supplying an electrical current to the unit substrate 7 (e.g. the connection section 10 including a first terminal 8 and a second terminal 9, the external connecting wire 11, the back-surface wire 19, the front-to-back wire connection section 20, and the like) from hindering light irradiation at the time of therapy. Further, in administering light treatment with the unit substrate the upper surface of the unit substrate 7 requires a spacer that keeps a constant distance from an affected part and fixes a positional relationship with the affected part. This makes it hard to provide the upper surface of the unit substrate 7 with an external wire connection. Therefore, the present embodiment configured such that the external connecting wire 11 can be drawn out from the lower surface of the unit substrate 7.

(Light Treatment Device)

As illustrated in FIG. 1, the light treatment device 1 is configured such that an electrical current supplied from the control and power source section 5 is distributed to each unit substrate 7 via the repeater 4 so that the plurality of unit substrates 7 can be used. The repeater 4 has only a function of distributing a predetermined constant current to each unit substrate 7. In the present embodiment, the repeater 4 is attached to the light irradiation substrate 2 and includes the plurality of constant-current elements 3 (including, for example, current-limit elements, which are elements that output an electrical current of a predetermined value in response to the supply of a large current). It should be noted that as many constant-current elements 3 as the unit substrates 7 to be driven are needed. In the case of the light treatment device 1, the constant-current elements 3 of the repeater 4 are connected in advance to the external connecting wires 11 of the respective unit substrates 7, and in detaching a unit substrate 7 from the light irradiation substrate 2, the external connecting wire 11 of the unit substrate 7 to be detached is disconnected from the repeater 4, so that the repeater 4 and the power source and control section 5 need only be connected in performing actual light irradiation.

The power source and control section 5 needs to control its output current according to the number of unit substrates 7 that are actually used. For example, in a case of driving five unit substrates 7 at 100 mA, the power source and control section 5 outputs a current of 500 mA, and five constant-current elements 3 rated at 100 mA output 100 mA to the five respective unit substrates 7. It should be noted that a unit substrate 7 does not necessarily need to be connected in advance to the repeater 4 before use and only the external connecting wire 11 of the unit substrate 7 to be used may be connected in advance to the repeater before use. It should be noted that, in this case, for greater convenience of connection to the repeater 4, it is preferable that the external connecting wire 11 be terminated with a socket, a plug, or the like to be easily connectable to the repeater 4.

Ideally, each unit substrate 7 has substantially the same light irradiation intensity. Therefore, it is preferable that a variation in light irradiation intensity of unit substrate 7 be 10% or less. Even with the inclusion of a unit substrate 7 having a variation of 10% in light irradiation intensity, each unit substrate 7 can be set at the same irradiation intensity by including a margin of about 10% in the irradiation time even with driving at the same electrical current.

In a case of using a plurality of unit substrates 7, it is necessary to consider the uniformity of light irradiation intensity at, the boundary between two adjacent unit substrates 7. In the present embodiment, by configuring a unit substrate 7 to, as mentioned above, include LED chips 13 arranged in an array so that, for example, the pitches Px between LED chips 13 in the X direction on the unit substrate 7 and the pitches Py between LED chips 13 in the Y direction on the unit substrate 7 are both 10 mm, the uniformity of light irradiation intensity within the unit substrate 7 is ensured. Meanwhile, by keeping these array pitches within the unit substrate 7 also at the boundary between two adjacent unit substrates 7, the uniformity of light irradiation intensity at the boundary between the two adjacent unit substrates 7 can be ensured. In the present embodiment, the center-to-center distance Dx between two adjacent LED chips 13 facing each other across the boundary between two unit substrates 7 adjacent to each other in the X direction and belonging to the respective unit substrates 7 and the center-to-center distance Dy between two adjacent LED chips 13 facing each other across the boundary between two unit substrates 7 adjacent to each other in the Y direction and belonging to the respective unit substrates 7 are both 10 mm.

As illustrated in FIGS. 1 and 3, the distance Ex between the boundary between two unit substrates 7 adjacent to each other in the X direction and the center of each of adjacent LED chips 13 facing each other across the boundary between two of the unit substrates 7 adjacent to each other in the X direction and belonging to the respective unit substrates 7 is substantially half of the center-to-center pitches Px between LED chips 13 adjacent to each other in the X direction within each of the unit substrates 7, and in the present embodiment, the distance Ex is 5 mm. Meanwhile, the distance Ey between the boundary between two unit substrates 7 adjacent to each other in the Y direction and the center of each of adjacent LED chips 13 facing each other across the boundary between two of the unit substrates 7 adjacent to each other in the Y direction and belonging to the respective unit substrates 7 is substantially half of the center-to-center pitches Py between LED chips 13 adjacent to each other in the Y direction within each of the unit substrates 7, and in the present embodiment, the distance Ey is 5 mm.

Ideally, the aforementioned distances Dx and Dy are set so that Distance Dx=Pitch Px and Distance Dy=Pitch Py. Therefore, the present embodiment is configured such that Distance Dx=Pitch Px=Distance Dy=Pitch Py=10 mm. However, there may be the need to secure an additional space in which to detach unit substrates 7 from each other or an additional space in which to connect unit substrates 7 to each other at the time of manufacture. In such a case, it is difficult for the distances Dx and Dy to maintain the relationships "Distance Dx=Pitch Px" and "Distance Dy=Pitch Py". Accordingly, in such a case, the uniformity of light irradiation intensity at the boundary between unit substrates 7 becomes reduced to a certain degree and it is necessary to allow for such a reduction to a certain degree. The allowable ranges are preferably "Distance Dx≤2×Pitch Px" and "Distance Dy≤2×Pitch Py". With the distances Dx and Dy falling within such ranges, a reduction in light irradiation intensity of the light irradiation substrate can be reduced to 30% or less. Therefore, irradiation with the required dose amount is made possible by making the light irradiation time 1.4 times as long. It should be noted that, in a case of considering concatenating unit substrates 7 in both the X and Y directions, it is necessary to satisfy both "Distance Dx≤2×Pitch Px" and "Distance Dy≤2×Pitch Py"; however, in a case of considering concatenating unit substrates 7 only in the X direction, it is only necessary to satisfy "Distance Dx≤2× Pitch Px", and in a case of considering concatenating unit substrates 7 only in the Y direction, it is only necessary to satisfy "Distance Dy≤2×Pitch Py".

(Spacer)

Performing light irradiation with the light treatment device 1 illustrated in FIG. 1 requires a spacer (see FIGS. 4 and 5) that keeps the distance between the light irradiation substrate 2 and an affected part. The spacer can be used in various forms such as a plastic bag processed to keep a certain thickness and filled with water or air, an epoxy or polyurethane flexible transparent resin plate, and a water-absorbing polymer processed into a plate. Bonding a resin plate or the like as such a spacer onto the upper surface of the light irradiation substrate 2 in advance makes it possible to more immediately irradiate the affected part with light.

Further, it is also possible to mount, for example, a temperature sensor, a light intensity sensor, or the like between the spacer and the affected part or an area of the skin around the affected part and control light irradiation power while monitoring the temperature measured the temperature sensor or the light intensity measured by the light intensity sensor or control light irradiation power with an output from the temperature sensor or the light intensity sensor.

In the present, embodiment, the spacer used is a resin plate roughly 10 mm thick formed from epoxy transparent low-viscosity resin (commercially available as CEP-10A from Nissin Resin Co., Ltd.) so that the affected part is covered by at least 10 mm. After this spacer has been placed on the affected part, the light irradiation substrate 2 is brought into intimate contact with a surface of the spacer so that the LED chips 13 face the affected part. In the present embodiment, a light coating of white petrolatum is applied to the affected part and the area therearound to bring the spacer into intimate contact with the affected part. Further, the same applies between the light irradiation substrate 2 and the spacer.

A relationship between the thickness T of the spacer and the distance D (pitches Px Py) between LED chips 13 within a unit substrate 7 is the key to the uniformization of light irradiation intensity on the affected part. It is necessary that at least 0.5≤(Thickness T/Distance D), and it is preferable that 0.8≤(Thickness T/Distance D). In a case where (Thickness T/Distance D) is smaller than 0.5, the light irradiation intensity in a position directly below an LED chip 13 is about twice as high as that in a position directly below the center of the space between LED chips 13. This undesirably makes the light irradiation intensity remarkably uneven. Therefore, the present embodiment is configured such that the thickness T of the spacer is 10 mm and (Thickness T/Distance D)=1.

(Examination of Effects of Light Treatment Device)

The light treatment device 1 illustrated in FIG. 1 was applied in performing light treatment with blue-violet light at a wavelength of 410 nm after infecting an ulcer formed in the back of a pig with methicillin-resistant *Staphylococcus aureus* (MRSA) and systemically administering 5-aminolevulinic acid (ALA). A part of ALA is converted into protoporphyrin IX (hereinafter referred to as "PpIX") in the bodies of MRSA. PpIX is photosensitizing substance and as degraded by the blue-violet light. At the time of degradation, active oxygen is generated. This active oxygen is believed to reduce MRSA by attaching MRSA. This method is expected to provide safe treatment aimed at antibiotic-resistant bacteria.

In the present examination of effects, two laboratory pigs were prepared. One of the pigs was made Sample A by forming a circular ulcer with a diameter of about 200 mm in the back of the pig and was infected with MRSA. The other pig was made Sample B by forming an elongated ulcer measuring about 20 mm by 60 mm in the back of the pig and was infected with MRSA. Both of the pigs were subjected to ARA administration and light irradiation.

As for the light irradiation, Sample A was irradiated with light by using, as a light irradiation substrate, one unit substrate 7 (40 mm by 40 mm) detached from a strictly-sterilized flexible substrate 6 composed of nine unit substrates 7, and Sample B was irradiated with light by using, as a light irradiation substrate, a combination (40 mm by 80 mm) of two unit substrates 7 detached from a strictly-sterilized flexible substrate 6 composed of nine unit substrates 7. Then, changes in size of the ulcers were observed in these states. It should be noted that since, in most cases, even light treatment devices need to be strictly sterilized in coping with diseases that involve the risk of infection, sterilization is performed in the present embodiment.

For Sample A, the power source and control section 5, which was a constant-current power source whose voltage can be boosted up to 55 V, and the unit substrate 7 were directly connected, and the unit substrate 7 was driven under a current of 50 mA. With attention paid to the temperature of the unit substrate 7, a dose amount of 50 J/cm$^2$ was attained in 20 minutes of irradiation. Meanwhile, for Sample B, the power source and control section 5, which was a constant-current power source whose voltage can be boosted up to 55 V, was connected to the repeater 4, which was then connected to the two unit substrates 7, and each of the unit substrates 7 was driven under a current of 50 mA. The repeater 4 includes a plurality of constant-current elements 3 each of which outputs 50 mA. The power source and control section 5 was turned on and off to control the two unit substrates 7 so that the two unit substrates 7 were turned on and off at the same timing. With attention paid to the temperature of each of the unit substrates 7, a dose amount of 50 J/cm$^2$ was attained in 20 minutes of irradiation.

After the procedure, the sizes of the ulcers in the two pigs (Samples A and B) were observed. The observation revealed that both of the pigs had their ulcers made clearly smaller each day. From the shrinkage of the ulcers as a whole, it can be estimated that an effect of killing MRAS substantially uniformly all over affected parts was brought about. All this showed that the application of the light treatment device 1 of the present embodiment makes it possible to effectively treat ulcers with light regardless of the size of the ulcers.

(Modifications)

In general, as illustrated in FIG. 3, the pitches Px between LED chips 13 in the X direction on the unit substrate 7 and the pitches Py between LED chips 13 in the Y direction on the unit substrate 7 are equal to each other. However, distributions of light output in the X and Y directions may be different from each other depending on the shape of the LED chips. In such a case, the pitches Px between LED chips in the X direction and the pitches Py between LED chips in the Y direction must be different from each other.

For example, elongated LED chips tend to easily emit light in a direction perpendicular to the long sides, i.e. from the long sides, and emit little light in a direction perpendicular to the short sides, i.e. from the short sides. In the case of LED chips of such a shape, the long sides are brighter than the short sides. Therefore, in a case where the long sides are parallel to the X axis, it is necessary that Pitch Px<Pitch Py, and in a case where the long sides are parallel to the Y axis, it is necessary that Pitch Px>Pitch Py. Further, since such a tendency of the light-emitting characteristics of LED chips may also be affected by the arrangement of electrodes, it is preferable that the pitches Px and Py be optimized according to the actual light-emitting characteristics of the LED chips.

It should be noted that in the case of roughly-rectangular LED chips in which the difference in length between the long sides and the short sides is 20% or less of the long sides, the difference in sight-emitting characteristic of the LED chips between the long sides and the short sides is not great; therefore, the LED chips can be simplistically thought of as being square in shape, and it is preferable that Pitch Px=Pitch Py within the unit substrate 7. For example, in case where blue-violet LED chips each having a size of 440 μm by 550 μm are used as in the case of Embodiment 1 described above, the difference in length between the long sides and the short sides is 20% or less of the long sides. Therefore, it is possible that Pitch Px=Pitch Py within the unit substrate 7.

Embodiment 2

In the following, a light irradiation substrate 2a according to another embodiment of the present invention is described with reference to FIGS. 4 and 5. For convenience of explanation, members having the same functions as those described above in Embodiment 1 are given the same reference signs and, as such, are not described below.

Figure 4:
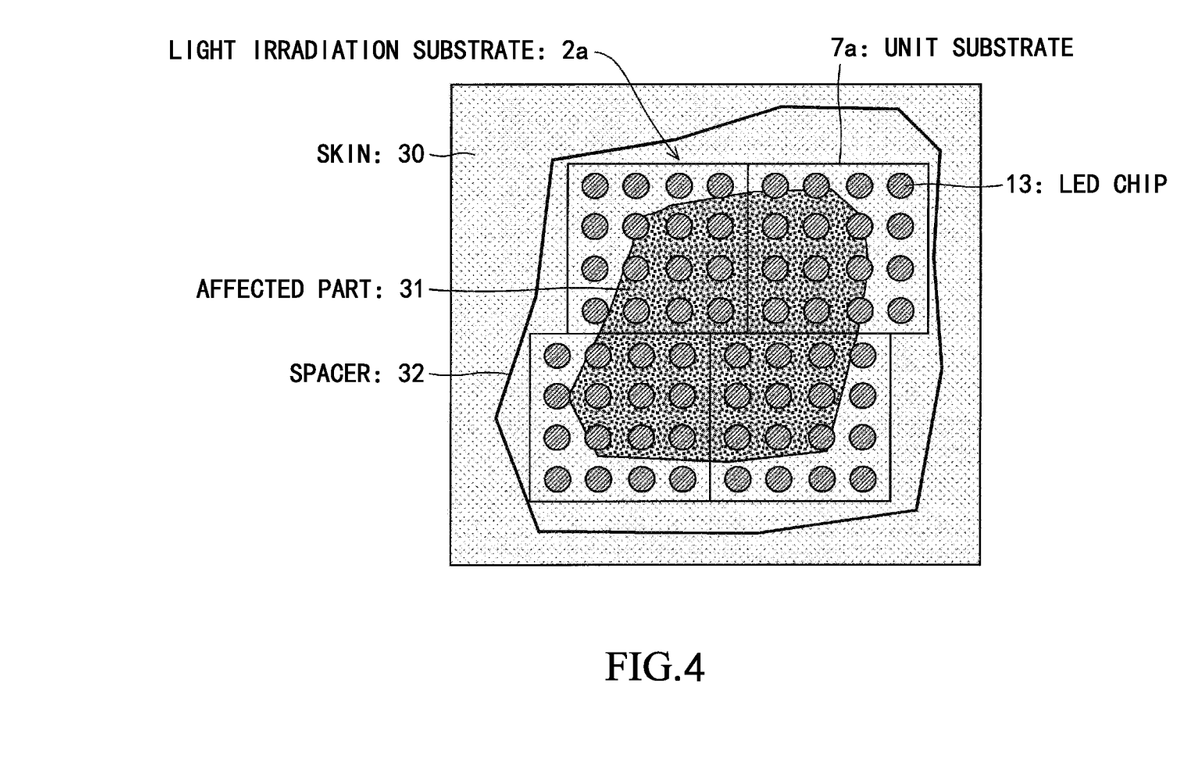
FIG. 4 illustrates a light irradiation substrate according to another embodiment of the present invention.
Figure 5:
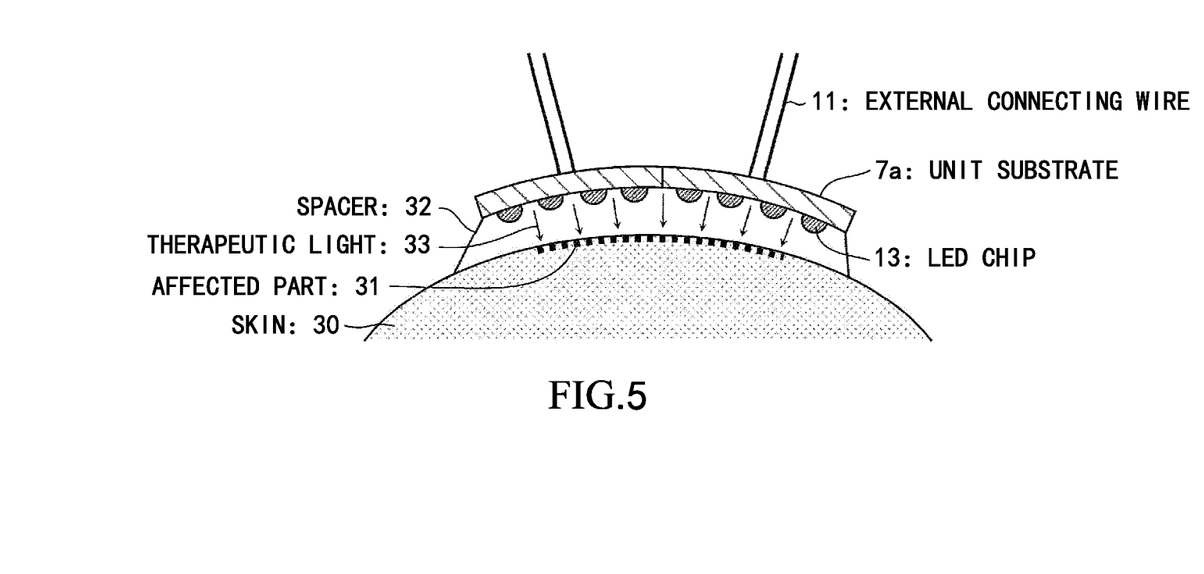
FIG. 5 is a cross-sectional view of the light irradiation substrate illustrated in FIG. 4.

FIGS. 4 and 5 illustrate a case where four already detached unit substrates 7a are used as a light irradiation substrate 2a in treating an affected part 31 of a skin 30 with light.

In the present embodiment, aimed at treating affected parts of larger area than Embodiment 1 described above, all of the unit substrates 7a are detached to serve as independent parts, and each of the unit substrates 7 is strictly sterilized. In most cases, even light treatment devices need to be strictly sterilized in coping with diseases that involve the risk of infection. Therefore, once detached, the unit substrates 7a are difficult to actually use without sterilization.

In Embodiment 1 described above, a flexible substrate 6 composed of nine unit substrates 7 is strictly sterilized first, and then unit substrates 7 detached from the sterilized flexible substrate 6 are used as a light irradiation substrate; therefore, unit substrates 7 not actually used are highly likely to be disposed of and end up being wasted.

To address this problem, a more efficient approach was made. In this approach, unit substrates 7a are detached from one another and subjected to normal cleaning first, and then the unit substrates 7 are sterilized so that they can be stored in a normal environment. Then, when needed, a combination of a needed number of the sterilized unit substrates 7 that have been stored can be tailored to an affected part.

It should be noted that, in the present embodiment, the flexible substrate used is a polyimide sheet measuring 80 mm per side and the polyimide sheet is composed of four unit substrates 7a each measuring 40 mm per side. Moreover, the flexible substrate has cuts formed in the X and Y directions by perforation so that two adjacent unit substrates 7a can be easily detached from each other at the boundary. Each of the unit substrates 7a has sixteen LED chips 13 mounted thereon. Moreover, the uniformity of light irradiation intensity within each of the unit substrates 7a is ensured by configuring the unit substrate 7a to have its LED chips 13 arranged in an array so that, for example, the pitches Px between LED chips 13 in the X direction on the unit substrate 7a and the pitches Py between LED chips 13 in the Y direction on the unit substrate 7 are both 10 mm. Meanwhile, the distance Ex between the boundary between two unit substrates 7a adjacent to each other in the X direction and the center of each of adjacent LED chips 13 facing each other across the boundary between the two unit substrates 7a adjacent to each other in the X direction and belonging to the respective unit substrates 7a and the distance Ey between the boundary between two unit substrates 7a adjacent to each other in the Y direction and the center of each of adjacent LED chips 13 facing each other across the boundary between the two unit substrates 7a adjacent to each other in the Y direction and belonging to the respective unit substrates 7a are each for example 4.5 mm.

It is for the following reason that the unit substrates 7a of the present embodiment are configured such that the distances Ex and Ey are 4.5 mm. Ideally, the distance Ex is ½ of the center-to-center distance Dx between two adjacent LED chips 13 facing each other across the boundary between two unit substrates 7a adjacent to each other in the X direction and belonging to the respective unit substrates 7a, and the distance Ex is ½ of the center-to-center distance Dy between two adjacent LED chips 13 facing each other across the boundary between two unit substrates 7a adjacent to each other in the Y direction and belonging to the respective unit substrates 7a. However, as illustrated in FIGS. 4 and 5, the positioning accuracy of placement with which unit substrates 7a are arranged in combination is not so high. Therefore, a little space may be left between adjacent unit substrates 7a. With consideration given to a space that may be left in this way, it is preferable that the distances Ex and Ey be slightly smaller than ½ of the distances Dx and Dy, respectively. Therefore, with consideration given to both the space and production tolerance, it is preferable that the ratio of (Distance Ex/Distance Dx) satisfy $0.7 \leq 2 \times Ex/Dx \leq 1.15$ and the ratio of (Distance Ey/Distance Dy) satisfy $0.7 \leq 2 \times Ey/Dy \leq 1.15$.

(Examination of Effects of Light Treatment Device)

In the present examination of effects, two laboratory pigs were prepared. One of the pigs was made Sample A by forming a circular ulcer with a diameter of about 200 mm in the back of the pig and was infected with MRSA. The other pig was made Sample C by forming an ulcer measuring about 60 mm by 70 mm in the back of the pig and was infected with MRSA. Both of the pigs were subjected to ARA administration and light irradiation.

As for the light irradiation, Sample A was irradiated with light by using a unit substrate 7a (40 mm by 40 mm) per se as a light irradiation substrate, and Sample C was irradiated with light by using, as a light irradiation substrate 2a, an arrangement of four unit substrates 7a placed as illustrated in FIGS. 4 and 5. Then, changes in size of the ulcers were observed in these states.

The spacer 32 used was a resin plate roughly 10 mm thick molded from epoxy transparent low-viscosity resin (commercially available as CEP-10A from Nissin in Resin Co., Ltd.) so that, the affected part was covered by at least 10 mm. After this spacer 32 had been placed on the affected part, the arrangement of four unit substrates 7a was placed on the spacer 32 and brought into intimate contact with the spacer 32 so that therapeutic light 33 from the LED chips 13 was directed toward the affected part. As illustrated in FIGS. 4 and 5, the four unit substrates 7a were placed so that they did not overlap each other and as little space as possible was left between them. It should be noted that, in the present embodiment, light coating of white petrolatum was applied to the affected part and the area therearound to bring the spacer 32 into intimate contact with the affected part. Further, the same applied between the unit substrates 7a and the spacer 32.

For Sample A, the power source and control section 5, which was a constant-current power source whose voltage can be boosted up to 55 V, and the unit substrate 7a were directly connected, and the unit substrate 7 was driven under a current or 50 mA. With attention paid to the temperature of the unit substrate 7a, a dose amount of 50 J/cm$^2$ was attained in 20 minutes of irradiation. Meanwhile, for Sample C, the power source and control section 5, which was a constant-current power source whose voltage can be boosted up to 55 V, and the repeater 4, which included four or more constant-current elements 3 with a rated current of 50 mA, were used. The repeater 4 was connected to the unit substrates 7a, and each of the unit substrates was driven under a current of 50 mA. It should be noted that since no consideration was given to variation in light irradiation intensity among the four unit substrates 7a, the power source and control section 5, which was a constant-current power source, was used to control the four unit substrates 7 so that the four unit substrates 7 were turned on and off at the same timing. With attention paid to the temperature of each of the two unit substrates 7a, a dose amount of 50 J/cm$^2$ was attained in 20 minutes of irradiation.

After the procedure, the sizes of the ulcers in the two pigs (Samples A and C) were observed. The observation revealed that both of the pigs had their ulcers made clearly smaller each day. From the shrinkage of the ulcers as a whole, it can be estimated that an effect of killing MRAS substantially uniformly all over the affected parts was brought about. All this showed that the application of a light treatment device including the light irradiation substrate 2a of the present embodiment makes it possible to effectively treat ulcers with light regardless of the size of the ulcers.

Embodiment 3

In the following, a light treatment device 1a according to another embodiment of the present invention is described with reference to FIG. 6. For convenience of explanation, members having the same functions as those described above in Embodiment 1 are given the same reference signs and, as such, are not described below.

Figure 6:
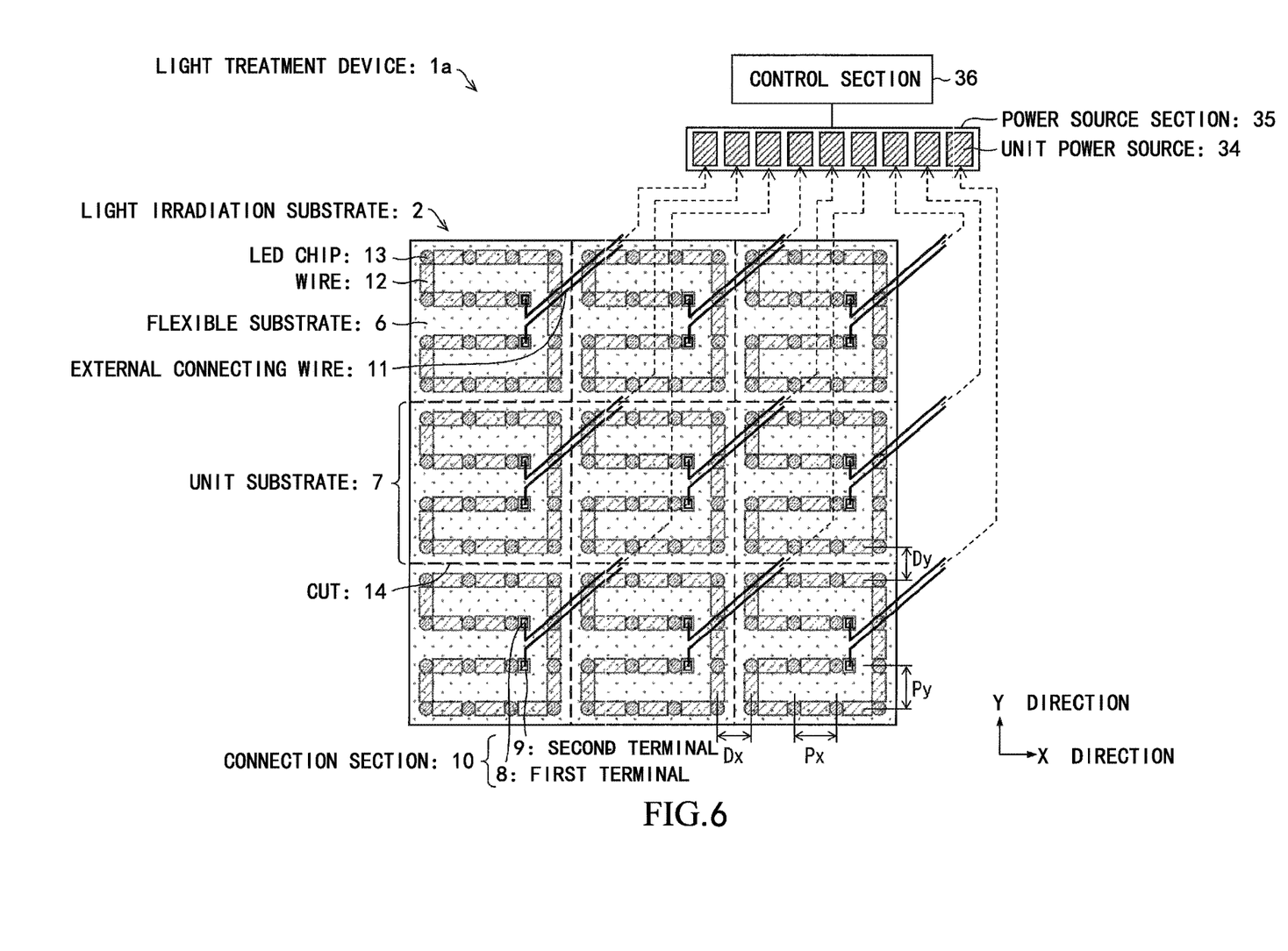
FIG. 6 schematically illustrates a configuration of a light treatment device according to still another embodiment of the present invention.

FIG. 6 schematically illustrates a configuration of the light treatment device 1a.

Embodiments 1 and 2 have described a case where the unit substrates 7 used have a variation of 10% or less in light irradiation intensity when driven at the same electrical current and each of the unit substrates 7 has substantially the same irradiation intensity. However, imposing strict restrictions on the variation in light irradiation intensity in the process of fabricating unit substrates 7 might lead to a reduction in fabrication yield of unit substrates 7 and a rise in fabrication cost of unit substrates 7.

To address this problem, the present embodiment makes it possible to further enhance the uniformity of light irradiation by measuring the light irradiation intensity of each unit substrate 7 at various driving current values in advance, storing, in a control section 36, the respective driving current values at which the nine unit substrates 7 give the same light irradiation intensity, and, in actual light irradiation, driving each of the unit substrates 7 at the corresponding driving current value.

As illustrated in FIG. 6, the light treatment device 1a includes a power source section 35 having a large number of unit power sources 34 whose driving current values are adjustable. It should be noted that, in the present embodiment, each of the unit substrates 7 is driven at a different driving current value optimized by the corresponding one of the unit power sources 34 and, therefore, the control section 35 controls the unit power sources 34 so that the unit substrates 7 are simultaneously turned on or off.

As illustrated in FIG. 6, the light treatment device 1a includes a power source section 35 having a large number of identical unit power sources 34 so that a plurality of unit substrates 7 can be used. It is only necessary to include as many unit power sources 34 as unit substrates 7, but with consideration given to a combination of an unseparated flexible substrate 6 and a unit substrate 7, it is possible to include more unit power sources 34 than unit substrates 7. One unit substrate 7 is connected to one unit power source 34, and the control section 35 is configured to control each unit power source 34. Therefore, the control section 35 is configured to control the unit substrates in parallel by controlling each unit power source 34.

It should be noted that although the present embodiment has been described by taking, as an example, a case where each of the unit substrates 7 is driven at a different driving current value optimized by the corresponding one of the unit power sources 34, the present embodiment is not limited to this example. For example, the unit substrates 7 may be driven at the same electrical current by the respective unit power sources 34, and the control section 35 may control the amount of current that is passed through each unit substrate and control the irradiation time or each of the unit substrates 7 by controlling the timing of turning on and turning off of the corresponding one of the unit power sources 34. Alternatively, for example in a case where an optical sensor is placed in the area around the affected part, the duration of light irradiation can be controlled according to its monitor.

[Conclusion]

A light irradiation substrate according to Aspect 1 of the present invention is a light irradiation substrate including: a flexible substrate composed of a plurality of unit substrates that are detachable; a plurality of light-emitting elements provided in a matrix on a first surface of the flexible substrate for each unit substrate; and wires through which electrical currents flow to each separate light-emitting element, the wires being provided on the first surface of the flexible substrate for each unit substrate, wherein a center-to-center distance between two adjacent light-emitting elements facing each other across a boundary between two of the unit substrates adjacent to each other in a first direction and belonging to the respective unit substrates is twice or less as long as a center-to-center distance between two light-emitting elements adjacent to each other in the first direction within each of the unit substrates, and each of the unit substrates includes a connection section that provides external connection of the wires, the connection section being provided on a second surface of the flexible substrate opposite to the first surface.

The foregoing configuration makes it possible to achieve a light irradiation substrate that is capable of optimum irradiation with therapeutic light regardless of the shape or size of affected parts at the lowest possible cost even in cases of emergency. Furthermore, the foregoing configuration makes it possible to achieve light treatment with reduced burden on users through efficient and uniform irradiation with therapeutic light while minimizing the side effects of irradiation with therapeutic light on normal sites that do not require irradiation with therapeutic light.

In Aspect 1, a light irradiation substrate according to Aspect 2 of the present invention is preferably configured such that a center-to-center distance between two adjacent light-emitting elements facing each other across a boundary between two of the unit substrates adjacent to each other in a second direction orthogonal to the first direction and belonging to the respective unit substrates is twice or less as long as a center-to-center distance between two light-emitting elements adjacent to each other in the second direction within each of the unit substrates.

According to the foregoing configuration, a reduction in uniformity of light irradiation intensity at the boundary between two of the unit substrates adjacent to each other in the second direction or the boundary between two of the unit substrates disposed to be adjacent to each other in the second direction after having been detached can be kept within a predetermined range. Therefore, the foregoing configuration can be easily used as a light irradiation substrate.

In Aspect 1 or 2, a light irradiation substrate according to Aspect 3 of the present invention is preferably configured such that a distance from a center of a light-emitting element provided outermost on the unit substrate to an outer edge of the unit substrate is substantially half of a center-to-center distance between two light-emitting elements adjacent to each other in a direction perpendicular to the outer edge of the unit substrate within the unit substrate.

According to the foregoing configuration, the light irradiation intensity at the boundary between two adjacent ones of the unit substrates or the boundary between two of the unit substrates disposed to be adjacent to each other after having been detached can be made substantially the same as that within each of the unit substrates.

In any one of Aspects 1 to 3, a light irradiation substrate according to Aspect 4 of the present invention may be configured such that the flexible substrate is separated into the unit substrates.

The foregoing configuration makes it possible to achieve a light irradiation substrate that is easily stored.

A light irradiation device according to Aspect 5 of the present invention is a light irradiation device including: the light irradiation substrate according to any one of Aspects 1 to 4; a power source section including a plurality of unit power sources; and a control section that adjusts an emission intensity of each of the unit substrates by controlling the power source section, wherein each of the unit substrates has a wire connected to a corresponding one of the plurality of unit power sources.

The foregoing configuration makes it possible to achieve a light irradiation device that is capable of optimum irradiation with therapeutic light regardless of the shape or size of affected parts at the lowest possible cost even in cases of emergency.

The present invention is not limited to the description of the embodiments above, but may be altered by a skilled person within the scope of the claims. An embodiment based on a proper combination of technical means disclosed in different embodiments is encompassed in the technical scope of the present invention.

INDUSTRIAL APPLICABILITY

The present invention is suitably applicable to a light irradiation substrate and a light irradiation device that irradiate an affected part of the skin of a human or an animal with light.

REFERENCE SIGNS LIST

1 Light treatment device (light irradiation device)
1a Light treatment device (light irradiation device)
2 Light irradiation substrate
3 Constant-current element
4 Repeater
5 Power source and control section
6 Flexible substrate
7 Unit substrate
7a Unit substrate 8 First terminal
9 Second terminal
10 Connection section
11 External connecting wire
12 Wire
13 LED chip (light-emitting element)
14 Cut
15 Bonding wire
16 LED protecting resin dome
17 Protective film
18 Connecting hole
19 Back-surface wire
20 Front-to-back wire connection section
21 Connection section seal
22 Back-surface reflective film
30 Skin
31 Affected part
32 Spacer
33 Therapeutic light
34 Unit power source
35 Power source section
36 Control section

The invention claimed is:

1. A light irradiation substrate comprising:
a flexible substrate including a plurality of unit substrates, the flexible substrate having cuts between two adjacent unit substrates of the plurality of unit substrates configured to permit detachment of the two adjacent unit substrates from each other;
a set of light-emitting elements including a plurality of light-emitting elements provided in a matrix on a first surface of the flexible substrate and on each of the plurality of unit substrates, including resin covered light emitting diodes configured to emit phototherapeutic light; and
a set of wires including a plurality of wires provided on the first surface of the flexible substrate and on each of the plurality of unit substrates, the plurality of wires electrically connected to the plurality of light-emitting elements, wherein
a center-to-center distance between two adjacent light-emitting elements facing each other across a boundary between two of the plurality of unit substrates adjacent to each other in a first direction is twice or less as long as a center-to-center distance between two light-emitting elements adjacent to each other in the first direction within each of the plurality of unit substrates, and
each of the plurality of unit substrates includes an external power connection section provided on a second surface of the flexible substrate opposite to the first surface and electrically connected to the plurality of wires, the external connection section configured to connect to an external power and control section so that each of the plurality of unit substrates is powered and controlled in parallel to any other unit substrate.

2. The light irradiation substrate according to claim 1, wherein
a center-to-center distance between two adjacent light-emitting elements facing each other across a boundary between two of the plurality of unit substrates adjacent to each other in a second direction orthogonal to the first direction is twice or less as long as a center-to-center distance between two light-emitting elements adjacent to each other in the second direction within each of the plurality of unit substrates.

3. The light irradiation substrate according to claim 1, wherein a distance from a center of a light-emitting element provided outermost on one of the plurality of unit substrates to an outer edge of the one of the plurality of unit substrates is half of a center-to-center distance between two light-emitting elements adjacent to each other in a direction perpendicular to the outer edge of the one of the plurality of unit substrates within the one of the plurality of unit substrates.

4. A light irradiation device comprising:
the light irradiation substrate according to claim 1;
wherein the external power and control section comprises:
a power source section including a plurality of unit power sources electrically connected to the plurality of unit substrates via a plurality of second wires, respectively; and
a control section that adjusts an emission intensity of each of the plurality of unit substrates by controlling the power source section.

* * * * *